United States Patent [19]

Torii et al.

[11] 4,219,393

[45] Aug. 26, 1980

[54] PROCESS FOR PRODUCING SULFENIMIDES

[75] Inventors: Sigeru Torii; Hideo Tanaka; Masashi Ukida, all of Okayama, Japan

[73] Assignee: Ouchi Shinko Kagaku Kogyo Kabushiki Kaisha, Tokyo, Japan

[21] Appl. No.: 22,891

[22] Filed: Mar. 22, 1979

[30] Foreign Application Priority Data

Mar. 24, 1978 [JP] Japan .................................. 53-32991

[51] Int. Cl.$^2$ ...................... C25B 3/02; C07D 213/48; C07D 209/34; C07D 210/00

[52] U.S. Cl. ..................................... 204/78; 546/296; 260/326 S; 260/326.5 S; 260/239.3 R; 260/239.3 A; 548/159; 548/168; 204/59 R

[58] Field of Search ..................... 546/296; 260/326 S, 260/326.5 S, 239.3 R, 239.3 A; 204/78, 59 R; 548/159, 168

[56] References Cited

U.S. PATENT DOCUMENTS 2,790,749   4/1957   Van der kerk et al. ......... 260/326 S

*Primary Examiner*—Henry R. Jiles
*Assistant Examiner*—Robert C. Whittenbaugh
*Attorney, Agent, or Firm*—Ladas, Parry, Von Gehr, Goldsmith & Deschamps

[57] ABSTRACT

Sulfenimides are prepared by electrolytic oxidation of organic disulfides or mercaptans and imides. The electrolytic oxidation is accelerated by a halide compound.

21 Claims, No Drawings

PROCESS FOR PRODUCING SULFENIMIDES

BACKGROUND OF THE INVENTION

1. Field of the Art

This invention relates to a novel process for producing sulfenimides and more particularly to a process for producing sulfenimides a characteristic feature of which is that a mixture comprising a disulfide or a mercaptan and an imide is subjected to an electrolytic oxidation in an organic solvent. The electrolytic oxidation is carried out preferably in the presence of a catalytic amount of a halogenated compound.

A series of the sulfenimides according to the present invention are important compounds for an inhibitor for premature vulcanization of rubber and have a reactivity for serving as a radical uptaking agent or a sulfenylating agent so that such compounds are expected to be used for various purposes.

2. Prior Art

The prior art teaches the producing of sulfenimides in generally the following two ways.

(1) M. Behforouz and J. E. Kerwood in *Journal of Organic Chemistry*, Vol. 34, P. 51 (1969), disclose producing a sulfenimide by reacting a sulfenyl chloride with an imide in the presence of a tertiary amine.

(2) K. H. Büchel and A. Conte in *Chemische Berichte*, Vol. 100, P. 1248 (1967) disclose producing a sulfenimide by reacting an N-bromimide with a disulfide.

These conventional processes, however, are accompanied by a number of problems from the viewpoint of the industrial synthesis such as the use of a large quantity of a chemically unstable or expensive reactant in the process and, further, the admixture of a halogenated compound into the product formed, whereby the stability of the product deteriorates in the process.

On the other hand, there has been no report relating to a direct synthesis of sulfenimides in a simple manner from the mixture comprising disulfides or mercaptans which are relatively easily available and imides.

SUMMARY OF THE INVENTION

In view of the difficulties in the prior art, it is an object of the present invention to provide a simple process for producing sulfenimides.

The present invention is based on our discovery that a sulfenimide is produced directly from a mixture of a disulfide or a mercaptan and an imide when an electric current is passed through a solution of the mixture in an organic solvent.

The present invention, in its broadest aspect, encompasses a process for producing a sulfenimide which comprises subjecting a mixture comprising an organic disulfide or a mercaptan and an organic imide in an organic solvent to electrolytic oxidation. In the preferred embodiment of the present invention, the electrolytic oxidation is carried out in the presence of a catalytic amount of a halide compound.

The reaction of the process according to this invention may be represented, for example, by the following equation:

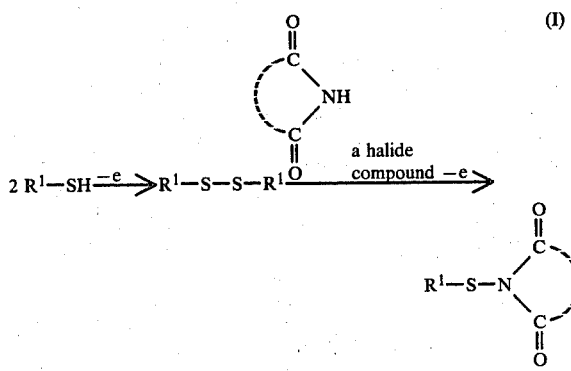

wherein $R^1$ is an alkyl or an aryl, and

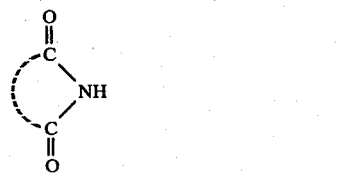

is a cyclic or chain imide.

In accordance with the present invention, a sulfenimide can be produced at an ambient temperature by merely supplying a necessary electric quantity through a suitable terminal voltage or current density to the mixture comprising the disulfide or mercaptan and the imide in the organic solvent preferably in the presence of a catalytic amount of the halide compound.

DETAILED DESCRIPTION OF THE INVENTION

Organic Disulfide

Examples of the organic disulfides which may be used for the process according to the present invention are organic compounds having the group —S—S— and include dialkyl disulfides such as di (trichloromethyl) disulfide, dimethyl disulfide, diethyl disulfide, dipropyl disulfide, diisopropyl disulfide, dibutyl disulfide, di-tert-butyl disulfide, diamyl disulfide, dicyclohexyl disulfide, dicyclooctyl disulfide, dicyclopentyl disulfide, and dicyclododecyl disulfide, aryl disulfides such as diphenyl disulfide, di(chloro)phenyl disulfide, di(nitro)phenyl disulfide, dibenzyl disulfide, ditolyl disulfide, dinaphthyl disulfide, and dibenzothiazyl disulfide.

The alkyl groups in the dialkyl disulfides which may be used in the present invention may be acyclic or cyclic and may contain from 1 to approximately 18, preferably from 1 to 6, carbon atoms for the acyclic alkyls and may contain from 3 to 12, preferably 6, carbon atoms for the cyclic alkyls. Cyclohexyl is preferred. The alkyls can have a substituent thereon which has no adverse effect on the electrolytic oxidation such as a halogen, e.g., chlorine.

The aryl groups in the aryl disulfides which may be used in the present invention may be phenyl, tolyl, naphthyl, or benzyl, or derivatives thereof wherein the phenyl or naphthyl moiety has a substituent thereon such as a lower alkyl having preferably up to 4 carbon atoms, a halogen, e.g. chlorine, or nitro. The "aryl" includes benzothiazyl.

Mercaptan

Examples of the mercaptans employed for the process of the production of sulfenimides according to the present invention include alkyl mercaptans such as trichloromethyl mercaptan, methyl mercaptan, ethyl mercaptan, propyl mercaptan, isopropyl mercaptan, butyl mercaptan, tert-butyl mercaptan, and amyl mercaptan as well as aryl mercaptans such as phenyl mercaptan, chlorophenyl mercaptan, nitrophenyl mercaptan, benzyl mercaptan, naphthyl mercaptan, and 2-mercaptovbenzothiazole.

The description on the alkyl and aryl groups given in terms of the organic disulfides applies here in terms of the mercaptans in view of their structures.

Imide

The imides are indicated by the formula:

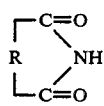

wherein R is (1) a bivalent saturated or unsaturated, acyclic or cyclic hydrocarbyl group having from approx. 2 to approx. 10 carbon atoms, (2) a bivalent saturated or unsaturated acyclic group having from 2 to approx. 6 carbon atoms and having —O— and/or —NH— linkage therein, or (3) a bivalent heterocyclic group having from approx. 6 to approx. 8 carbon atoms including those containing an oxabicyclo structure. Examples of such imides include phthalimide, naphthalimide, succinimide, adipimide, glutarimide, maleimide, 4-cyclohexene-1,2-dicarboimide, hydantoin, 2,3- or 3,4-pyridine dicarboimide, 7-oxabicyclo-[2,2,1]heptane-2,3-dicarboimide, and the like.

The most typical imides are intramolecular imides of dicarboxylic acids, which are cyclic imides. In view of the stability or ease of formation of the cyclic structure the cyclic imides may be of 5- to 7-membered ring. Accordingly, the dicarboxylic acids are succinic, glutaric, adipic, maleic acids or derivatives thereof substituted with a lower alkyl group such as having 1 to 4 carbon atoms; and phthalic and naphthalic acids or derivatives thereof substituted with a lower alkyl. These dicarboxylic acids can have a substituent thereon which has no adverse effect on the electrolytic oxidation such as chlorine.

Organic Solvent

The production of sulfenimides by the electrolytic oxidation reaction according to the present invention is carried out in an organic solvent. Examples of the organic solvents which may be used in the process of this invention include nitriles such as acetonitrile, propionitrile, and butyronitrile; amides such as N,N-dimethylformamide, and N,N-dimethylacetamide; alcohols such as methanol, ethanol, propanol, and buthanol; halohydrocarbons such as dichloromethane, chloroform, and 1,2-dichloroethane; and ethers such as diglyme, monoglyme, dioxane, methylcellosolve, and 15-crown-5. In the present invention, the organic solvent such as those given hereinabove may be used singly or in combination with each other. The preferable solvent is an aprotic solvent such as a nitrile and/or an ether or a mixture of a major quantity of an aprotic solvent and a minor quantity of a protic solvent such as an alcohol, and those particularly preferable are acetonitrile and mixtures comprising acetonitrile as the principal constituent and one or more of the ethers. Furthermore, it is to be noted that even if the above organic solvent contains a small amount of moisture, it may be employed in the process of the present invention, although there is some difference dependent on the types of the solvents, the types of the halide compounds when used as a catalyst, and the types of supporting electrolytes when used.

The solvent should preferably be selected so that at least one of the reactants and the product is soluble therein.

Halide Compound

The electrolytic oxidation reaction according to this invention may be carried out without employing a halide compound as a catalyst. The current efficiency as well as the yield of sulfenimides will, however, be increased when the electrolytic oxidation reaction is carried out in the presence of the halide compound.

Examples of the halide compounds which may be employed in the process of the present invention include chloride compounds, bromide compounds, and iodide compounds which are inorganic or organic.

(1) Examples of such chloride compounds include alkali metal chlorides such as lithium chloride, sodium chloride, and potassium chloride; alkaline earth metal chlorides such as magnesium chloride, calcium chloride, strontium chloride, and barium chloride; ammonium chloride; hydrochloric acid; quaternary ammonium chlorides such as tetramethylammonium chloride, tetraethylammonium chloride, tetrapropylammonium chloride, and tetrabutylammonium chloride.

(2) Examples of the bromide compounds include alkali metal bromides such as lithium bromide, sodium bromide, and potassium bromide; alkaline earth metal bromides such as magnesium bromide, calcium bromide, strontium bromide, and barium bromide; ammonium bromide; hydrobromic acid, other bromides of various metals; quaternary ammonium bromides such as tetramethylammonium bromide, tetraethylammonium bromide, tetrapropylammonium bromide, and tetrabutylammonium bromide.

(3) Examples of iodide compounds include alkali metal iodides such as lithium iodide, sodium iodide, and potassium iodide; alkaline earth metal iodides such as magnesium iodide, calcium iodide, strontium iodide, and barium iodide; ammonium iodide; hydroiodic acid; quaternary ammonium iodides such as tetramethylammonium iodide, tetraethylammonium iodide, tetrapropylammonium iodide, and tetrabutylammonium iodide.

The preferable halide compounds are alkali metal, alkaline earth metal, ammonium, and quaternary ammonium halides, and the more preferable halide compounds are alkali metal bromides, and the most preferable one is sodium bromide.

Supporting Electrolyte

In the process according to the present invention, it is not required to add a supporting electrolyte other than the above-mentioned halide compounds, but amines, ammonium salts, inorganic salts and the like which are used in an ordinary electrolytic oxidation reaction may also be added. Examples of supporting electrolytes include amines, preferably tertiary amines, such as triethylamine, tripropylamine, and pyridine; quaternary ammonium salts such as tetramethylammonium salt, and tetraethylammonium salt; perchlorates preferably alkali metal perchlorates or quaternary ammonium perchlorates such as lithium perchlorate, sodium perchlorate, and tetraethylammonium perchlorate; and inorganic salts of sulfuric acid, and sodium hydroxide.

Use of a supporting electrolyte in electrolytic oxidation is known in the art, and the use of a supporting electrolyte in the present process is carried out in accordance with the conventional practice.

Electrode

The electrodes which may be used in the production of sulfenimides by the electrolytic oxidation reaction according to this invention include an ordinary electrolytic electrode, and it is preferable to use platinum electrode, stainless steel electrode, or carbon electrode.

Manner of Practice

The mode of reducing the present invention to practice will now be described.

Into an electrolytic cell equipped with a heating device, a stirrer, a thermometer, and in addition, two electrodes placed in parallel to each other with a suitable distance, 1 mol equivalent of the imide is charged and further, from 0.1 to 10 mol equivalent, preferably from 0.2 to 2 mol equivalent of the disulfide or the mercaptan are charged with respect to 1 mol equivalent of the imide. The organic solvent or a solvent comprising principally the organic solvent is then added to the resulting mixture in an amount corresponding to that within a range of from 2 to 5000 times, preferably from 5 to 500 times of the disulfide or the mercaptan in the weight ratio. Furthermore, the halide compound is added to the mixture in an amount corresponding to either one within a range of from 0 to 1 time, preferably from 0.01 to 0.2 time of the disulfide or the mercaptan, or one within a range of from 0 to 1 mol equivalent, preferably from 0.001 to 0.05 mol equivalent to 1 liter of the solvent, and in this case, even if the halide compound does not dissolve easily in the solvent, the resultant mixture can be employed as it is. The imide is usually used in an amount of 0.001 to 10 mol per 1 liter of the organic solvent.

The condition of the electrolytic reaction is varied dependent on the shapes of the electrolytic cells, the types of the disulfides or mercaptans, or the types of the imides, the types of the halide compounds, and the types of the organic solvents. The temperature at the time of the electrolytic reaction is generally within a range of from 0° to 100° C., preferably a range of from 0° to 50° C., more preferably a range of from 10° to 50° C. The methods of the electrolytic reaction include a usual method for regulating electric current, a method for regulating electric potential, and an electrolyzing method wherein the terminal voltage is kept constant. In any of these cases, the product to be prepared can be obtained in a quantitative yield by passing electric current at substantially the theoretical quantity of electricity (2F/mol:disulfide basis) in keeping the current density generally from 0.1 to 500 mA/cm², preferably from 0.1 to 300 mA/cm², more preferably from 0.2 to 200 mA/cm². Depending on the types of the organic solvents used and the like, there are some cases in which the current efficiency decreases, but in this case, if a quantity of electricity which is greater than that of the theoretical value is caused to flow, the product to be produced can be obtained in a high yield. The terminal voltage is usually in the range of 1 to 50 volts.

After completion of the electrolytic reaction, the solvent is distilled off, and the product thus obtained is subjected to required after-treatments such as purification and the like thereby to obtain a final, finished product.

Since conventional processes for the production of sulfenimides relate to a pure chemical reaction, such reaction is inevitably accompanied by side reactions, and, therefore, there is a disadvantage in that a draining treatment due to the products by the side reactions is required.

On the other hand, according to the process of the present invention, the reaction can easily be carried out at a temperature near the room temperature, and sulfenimides may be produced in a high yield by employing no oxidizing agent, acid, base, and the like. In addition, there is an outstanding characteristic feature in that the process is the one which is not accompanied by environmental pollution. Accordingly, the process of the present invention not only relates to an art for producing sulfenimides through which the conservation of environment can be amply attained but also has a characteristic feature of saving resources or saving energy, so that the process is very economical and suitable for industrial production of sulfenimides.

The process of the instant invention will be illustrated hereinbelow in more detail by the following examples, but it is to be understood that the invention is not limited to these examples.

Example 1

Into a 50-ml test tube with a side arm equipped with a magnetic stirrer, a thermometer, and platinum electrodes (2 cm×33 cm), the spacing between which was 7 mm, 468 mg (2.03 millimol) of dicyclohexyl disulfide, 650 mg (4.42 millimol) of phthalimide, 11 mg (0.11 millimol) of sodium bromide, and 200 mg of the supporting electrolyte of tetraethylammonium perchlorate were charged, and further, 20 ml of acetonitrile was added thereto as the solvent. These materials were stirred to prepare a mixture. The mixture was then subjected to an electrolysis at a terminal voltage of 3 volts and a current density of from 1.7 to 0.3 mA/cm² for 18 hours while the reaction temperature was maintained at 20° C. After 2.37 F/mol (disulfide basis) of the quantity of electricity was passed through the mixture, the solvent was distilled off under a reduced pressure, and thereafter, benzene was added to the remaining materials thereby to remove the insoluble substances. The filtrate was concentrated and purified by passing it through a silica gel column by the use of benzene as the developer solvent, whereupon 1,050 mg (yield 99%) of N-(cyclohexylthio) phthalimide to be prepared was obtained. The melting point of the resultant product was 92°–93° C., and it was confirmed that the product was N-(cyclohexylthio) phthalimide by identification by both infrared spectrum and nuclear magnetic resonance spectrum.

| | |
|---|---|
| Infrared Spectrum (Nujol) | 1780, 1740, 1730, 1704, 1608, 1280, 1260, 860, 708 cm$^{-1}$ |
| Nuclear Magnetic Resonance Spectrum (CDCl$_3$) | $\delta$1.00–2.30 (m, 1 CH, CH$_2$), 2.70–3.50 (Broad, 1 H, CH—S), 7.60–8.20 (m, 4H, CH) |

Examples 2-10

The procedure set forth in Example 1 was carried out except that the halide compound as well as the electrolyzing condition in Example 1 were modified as shown in the following Tables 1 and 2. The results obtained are indicated respectively in the same Tables.

Example 11

The procedure in Example 1 was carried out except for the use of a hydrous acetonitrile consisting of 20 ml of acetonitrile and 0.2 ml of water in place of 20 ml of the solvent of acetonitrile in Example 1 and for the modification of the electrolyzing condition as indicated in the following Table 3. The results obtained are shown in the same Table.

Example 12

The procedure as in Example 1 was carried out except for the use of mercaptan in place of the disulfide of Example 1 and the modification of the electrolyzing condition as indicated in the following Table 4. The results obtained are shown in the same Table.

Examples 13-14

The procedure in Example 1 was carried out except for the change of the quantity of the phthalimide to 325 mg (2.21 millimol), the use of stainless steel electrodes (2 cm $\times$ 3 cm) as the electrodes, and the modification of the electrolyzing conditions as indicated in the following Table 5. The results obtained are shown in the same Table.

Examples 15-17

The procedure in Example 1 was carried out except for the replacement of the electrodes of Example 1 by carbon electrodes (2 cm $\times$ 3 cm) and the modification of the electrolyzing conditions as indicated in the following Table 6. The results are shown in the same Table.

Table 1

Relationship between the amount of sodium bromide and the yield by electrolysis

| Example No. | Dicyclohexyl disulfide [mg(millimol)] | Phthalimide [mg(millimol)] | Sodium bromide (mg) | Current (mA) | Reaction period (hour) | Quantity of electricity [F/mol (disulfide basis)] | Sulfenimides N-(cyclohexylthio) phthalimide yield (mg) | Yield (%) |
|---|---|---|---|---|---|---|---|---|
| 2 | 467 [2.03] | 1,000 [6.80] | 50 | 10→5 | 20 | 3.31 | 935 | 88 |
| 3 | 483 [2.10] | 650 [4.42] | 20 | 9→(5→15)→3 | 23.5 | 3.35 | 967 | 88 |
| 1 | 468 [2.03] | 650 [4.42] | 11 | 9→1.5 | 18 | 2.37 | 1,050 | 99 |
| 4 | 473 [2.05] | 650 [4.42] | 1 | 70→2 | 23.5 | | 762 | 71 |
| 5 | 461 [2.00] | 900 [6.00] | — | 24→2 | 46 | | 177 | 17 |

Note:
The conditions in the above examples were the same as those of Example 1 except as shown in the above Table 1 and except for the modification of the reaction temperature to 15° to 23° C.

Table 2

Relationship between various bromide compounds and the yields by electrolysis

| Example No. | Dicyclohexyl disulfide [mg (millimol)] | Phthalimide [mg (millimol)] | Bromide compound (mg) | Current (mA) | Reaction period (hour) | Quantity of electricity [F/mol (disulfide basis)] | Sulfenimides N-(cyclohexylthio) phthalimide Yield (mg) | Yield (%) |
|---|---|---|---|---|---|---|---|---|
| 2 | 467 (2.03) | 1,000 (6.80) | Sodium bromide 50 | 10→5 | 20 | 3.31 | 935 | 88 |
| 6 | 486 (2.11) | 1,000 (6.80) | Lithium bromide 50 | 30→4 (4→18→30→19) | 22.5 | 7.83 | 946 | 86 |
| 7 | 483 (2.10) | 1,000 (6.80) | Potassium bromide 60 | 26→4 | 24 | 3.62 | 878 | 80 |
| 8 | 499 (2.16) | 1,000 (6.80) | Magnesium bromide 60 | 38→6 | 20 | 6.22 | 880 | 77 |
| 9 | 478 (2.07) | 1,000 (6.80) | Tetraethylammonium bromide 105 | 65→5 | 20 | 10.8 | 805 | 75 |
| 10 | 464 (2.01) | 1,000 (6.80) | Ammonium bromide 50 | 45→3.5 | 20 | 9.2 | 750 | 71 |

Note: The conditions in the above examples were the same as those of Example 1 except as indicated in the above Table 2.

Table 3

The yield of sulfenimides by electrolysis in hydrous acetonitrile

| Example No. | Dicyclohexyl disulfide [mg (millimol)] | Phthalimide [mg (millimol)] | Sodium bromide (mg) | Current (mA) | Reaction period (hour) | Quantity of electricity [F/mol (disulfide basis)] | Sulfenimides N-(cyclohexylthio) phthalimide Yield (mg) | Yield (%) |
|---|---|---|---|---|---|---|---|---|
| 11 | 570 (2.47) | 1,000 (6.80) | 60 | 42→10 | 22 | 4.23 | 900 | 72 |

Note: The conditions of Example 11 were the same as those of Example 1 except as shown in the above Table 3 and except that 20 ml of acetonitrile of the solvent in Example 1 was replaced by a hydrous acetonitrile consisting of 20 ml of acetonitrile and 0.2 ml of water.

Table 4

The yield of sulfenimides by electrolysis in which mercaptan is employed

| Example No. | Cyclohexyl mercaptan [mg (millimol)] | Phthalimide [mg (millimol)] | Sodium bromide (mg) | Current (mA) | Reaction period (hour) | Quantity of electricity [F/mol (disulfide basis)] | Sulfenimides N-(cyclohexylthio) phthalimide Yield (mg) | Yield (%) |
|---|---|---|---|---|---|---|---|---|
| 12 | 475 (4.09) | 660 (4.49) | 21 | 26→4 | 26 | 1.40 | 827 | 77 |

Note: The conditions in Example 12 were the same as those of Example 1 except as indicated in Table 4.

Table 5

The yields of sulfenimides by electrolysis in which various disulfides are employed

| Example No. | Disulfides [mg (millimol)] | Terminal voltage (volt) | Current (mA) | Reaction period (hour) | Quantity of electricity [F/mol (disulfide basis)] | Sulfenimides | Yield (mg) | Yield (%) |
|---|---|---|---|---|---|---|---|---|
| 13 | Diphenyl disulfide 439 (2.05) | 3.5 | 20→2 | 18 | 2.69 | N-(phenylthio) phthalimide | 954 | 93 |
| 14 | Dibenzyl disulfide 493 (2.00) | 3.5 | 25→1 | 20 | 2.80 | N-(benzylthio) phthalimide | 1,009 | 94 |

Note: The conditions of the above examples were the same as those of Example 1 except as set forth in the above Table 5 and except that the amount of the phthalimide was changed to 325 mg (2.21 millimol), and stainless steel electrodes (2 cm × 3 cm) were used as the electrodes.

Table 6

The yields of N-sulfenyl succinic acid imides by electrolysis in which various disulfides are employed.

| Example No. | Disulfides [mg (millimol)] | Succinimide [mg (millimol)] | Terminal voltage (volt) | Current (mA) | Reaction period (hour) | Quantity of electricity [F/mol (disulfide basis)] | Sulfenimides | Yield (mg) | Yield (%) |
|---|---|---|---|---|---|---|---|---|---|
| 15 | Dicyclohexyl disulfide 462 (2.00) | 440 (4.44) | 3.0 | 20→1 | 21 | 2.95 | N-(cyclohexylthio) succinimide | 851 | 99 |
| 16 | Diphenyl disulfide 437 (2.00) | 440 (4.44) | 3.5 | 22→8 | 22 | 6.16 | N-(phenylthio) succinimide | 777 | 94 |
| 17 | Dibenzyl disulfide 493 (2.00) | 440 (4.44) | 3.0 | 10→2 | 22 | 3.36 | N-(benzylthio) succinimide | 825 | 93 |

Note: The conditions of the above examples were the same as those of Example 1 except as indicated in the above Table 6 and except that the electrodes of Example 1 were replaced by carbon electrodes (2 cm × 3 cm).

Example 18

Into a 50-ml test tube with a side arm equipped with a magnetic stirrer, a thermometer, and platinum electrodes (2 cm × 3 cm), the spacing between which was 7 mm, 468 mg (2.03 millimol) of dicyclohexyl disulfide, 650 mg (4.42 millimol) of phthalimide, and 11 mg (0.11 millimol) of sodium bromide were charged, and further, 20 ml of acetonitrile and 2 ml of diglyme were added thereto as the solvent. These materials were stirred to prepare a mixture. The mixture was then subjected to an electrolysis at a terminal voltage of 3 volts and a current density of 1.5 to 0.3 mA/cm$^2$ for 18 hours while the reaction temperature was maintained at 20° C. After 2.37 F/mol (disulfide basis) of the quantity of electricity was passed through the mixture, the solvent was distilled off under a reduced pressure, and the residue was filtered to give a precipitate. The precipitate thus obtained was washed with water and dried to give 1048 mg (yield 98.9%) of a white crystalline product. The product had a melting point of 90.5° to 91.8° C. and was found to be the same as the product obtained in Example 1 through mixed examination.

Examples 19–24

The procedure set forth in Example 18 was carried out except that various disulfides and phthalimides other than those used in Example 1 were subjected to electrolysis. The results obtained are indicated in Table 7.

Identification of the products obtained was made by determination of the melting points thereof, which were compared with those given in Mohammad Behforouz and Joseph E. Kerwood: J. Org. Chem. Vol. 34, 52(1969).

Examples 25-26

The procedure set forth in Example 18 was carried out except that 459 mg (4.42 millimol) of glutarimide in place of phthalimide, and 2.03 millimol each of diphenyl disulfide and dibenzyl disulfide as the disulfide were used. The results obtained are indicated in Table 8.

Identification of the products obtained was made by determination of melting points thereof, which were compared with those given in Karl Heinz Büchel and Appollonio Conte: Chem. Ber. Vol. 100, 1250 (1967).

Examples 27-29

The procedure set forth in Example 18 was carried out except that 658 mg (4.42 millimol) of tetrahydrophthalimide in place of phthalimide and 2.03 millimol of various disulfides in place of dicyclohexyl disulfide were used. The results obtained are indicated in Table 9.

Identification of the products were made in accordance with the procedure set forth in Examples 19-24.

ganic solvent preferably in the presence of the halide compound, thereby producing the product to be prepared. Therefore, it is obvious that the steps of the reaction are simple, and there arises no side reaction so that the sulfenimides of a good quality can be obtained.

What is claimed is:

1. A process for producing a sulfenimide which comprises subjecting a mixture of an imide of the formula:

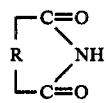

wherein R is (1) a bivalent saturated or unsaturated, acyclic or cyclic hydrocarbyl group having from approximately 2 to approximately 10 carbon atoms, (2) a bivalent saturated or unsaturated acyclic group having from 2 to approximately 6 carbon atoms and having —O— and/or —NH— linkage therein, or (3) a bivalent heterocyclic group having from 6 to 8 carbon atoms including those containing an oxabicyclo structure with an organic disulfide selected from the group consisting of dialkyl disulfide wherein each alkyl group is acyclic of from 1 to 18 carbon atoms or is cyclic of 3 to 12 carbon atoms optionally substituted with a halo atom Table 7

Synthesis of sulfenimides by electrolytic reaction of phthalimide and various disulfides

| Example No. | Disulfides | Terminal voltage (V) | Current (mA) | Quantity of electricity (F/mol) | Sulfenimides M.P.(°C.) | M.P.(lit.) | Yield (%) |
|---|---|---|---|---|---|---|---|
| 19 | Di(m-tolyl)disulfide | 3.0 | 22→2 | 2.30 | 135.5-137.0 | 138-139 | 92 |
| 20 | Di(p-chlorophenyl)disulfide | 3.0 | 20→2 | 2.31 | 179-180 | 179-180 | 90 |
| 21 | Dilauryl disulfide | 3.0 | 22→4 | 2.10 | 64.5-66.0 | 64.0-64.5 | 95 |
| 22 | Diethyl disulfide | 3.0 | 24→3 | 2.15 | 112.5-114.0 | 115 | 88 |
| 23 | Di-t-butyl disulfide | 3.0 | 23→2 | 2.05 | 129-130 | 130-131 | 94 |
| 24 | Di-(α-chlorocyclohexyl)disulfide | 3.0 | 22→2 | 2.21 | 119-120.5 | 121-122 | 85 |

Table 8

| Example No. | Disulfides | Terminal voltage (V) | Current (mA) | Quantity of electricity (F/mol) | Sulfenimides M.P.(°C.) | M.P.(lit.) | Yield (%) |
|---|---|---|---|---|---|---|---|
| 25 | Diphenyl disulfide | 3.0 | 20→4 | 3.58 | 96-97.5 | 95-96 | 93.3 |
| 26 | Dibenzyl disul- | 3.0 | 20→3 | 2.41 | 106.5-108 | 106-107 | 91.5 |

Table 9

| Example No. | Disulfides | Terminal voltage (V) | Current (mA) | Quantity of electricity (F/mol) | Sulfenimides M.P.(°C.) | M.P.(lit.) | Yield (%) |
|---|---|---|---|---|---|---|---|
| 27 | Diphenyl disulfide | 3.0 | 22→3 | 2.95 | 120-121.5 | 121-122.5 | 92 |
| 28 | di(p-chlorophenyl)disulfide | 3.0 | 21→3 | 2.23 | 146-147 | 147-148 | 89 |
| 29 | Dicyclohexyl disulfide | 3.0 | 24→4 | 2.20 | 89-90.5 | 90-91.5 | 97 |

As is apparent from the above examples, the process for producing sulfenimides according to the present invention relates to the one in which the mixture comprising the disulfide or the mercaptan and the imide is directly subjected to electrolytic oxidation in the orand diaryl disulfides wherein each aryl group is phenyl, tolyl, naphthyl, benzyl, or is a substituted phenyl or naphthyl group wherein said substituent is an alkyl group of up to 4 carbon atoms, a halo atom or a nitro group or is benzothiazyl, or with a mercaptan selected from the group consisting of alkyl mercaptans of 1 to 5 carbon atoms, trichloromethyl mercaptan, phenyl mercaptan, chlorophenyl mercaptan, nitrophenyl mercaptan, benzyl mercaptan, naphthyl mercaptan and 2-mercaptobenzothiazole, to electrolytic oxidation in an organic solvent selected from the group consisting of aprotic polar solvents and mixtures of a major quantity of aprotic polar solvent and a minor quantity of polar solvent or water.

2. A process according to claim 1, wherein said electrolytic oxidation is carried out in the presence of a catalytic amount of a compound which is capable of producing a halide ion.

3. A process according to claim 1 or 2 wherein said electrolytic oxidation is carried out by employing a pair of electrodes selected from the group consisting of platinum electrodes, stainless steel electrodes, and carbon electrodes.

4. A process according to claim 1 or 2 wherein said electrolytic oxidation is carried out at a terminal voltage within a range of from 1 to 50 volts.

5. A process according to claim 1 or 2 wherein said electrolytic oxidation is carried out at a current density within a range of from 0.1 to 300 mA/cm$^2$.

6. A process according to claim 1 or 2 wherein said electrolytic oxidation is carried out at a temperature within a range of from 0° to 50° C.

7. A process according to claim 1 or 2 wherein said organic solvent is acetonitrile.

8. A process according to claim 2 wherein said halide compound is selected from the group consisting of alkali metal chlorides, bromides and iodides; alkaline earth metal chloride, bromide and iodide; ammonium chloride, bromide and iodide; and quaternary ammonium chlorides, bromides and iodides.

9. A process according to claim 8 wherein said halide compound is an alkali metal bromide.

10. A process according to claim 9 wherein said halide compound is employed in such an amount that said halide compound is within a range of from 0 to 1 mol with respect to 1 mol of said imide.

11. A process according to claim 10 wherein said disulfide is employed in an amount such that said disulfide is within a range of from 0.2 to 2 mol with respect to 1 mol of said imide.

12. A process according to claim 10 wherein said mercaptan is employed in an amount such that said mercaptan is within a range of from 0.2 to 2 mol with respect to 1 mol of said imide.

13. A process according to claim 11 or 12 wherein said imide is employed in an amount such that said imide is within a range of from 0.001 to 10 mol with respect to 1 liter of said organic solvent.

14. A process according to claim 2 wherein said organic disulfide is selected from the group consisting of dialkyl disulfides having 1 to 18 carbon atoms in the alkyls, and aryl disulfides having as the aryl moiety a member selected from the group consisting of phenyl, tolyl, naphthyl and benzothiazyl.

15. A process according to claim 14 wherein said alkyl moiety has a chloro-substituent.

16. A process according to claim 14 wherein said aryl moiety has a substituent selected from the group consisting of chloro- and nitro-.

17. A process according to claim 1 or 2 wherein said mercaptan is selected from alkyl mercaptans having 1 to 18 carbon atoms in the alkyl, and aryl mercaptans having as the aryl moiety a member selected from the group consisting of phenyl, tolyl, naphthyl and benzothiazyl.

18. A process according to claim 17 wherein said alkyl moiety has a chloro-substituent.

19. A process according to claim 17 wherein said aryl moiety has a substituent selected from the group consisting of chloro- and nitro-.

20. A process according to claim 1 or 2 wherein said imide is intramolecular imide of a dicarboxylic acid selected from the group consisting of succinic, glutaric, adipic, maleic, phthalic and naphthalic acids.

21. A process according to claim 2 wherein said organic disulfide is a dialkyl disulfide having 1 to 6 carbon atoms, said imide is phthalimide, said halide compound is an alkali metal bromide and said organic solvent comprises acetonitrile.

* * * * *